(12) United States Patent
Kwon et al.

(10) Patent No.: US 7,851,479 B2
(45) Date of Patent: Dec. 14, 2010

(54) USE OF PYRIMIDINEDIONE DERIVATIVE FOR PREVENTING OR TREATING HEPATITIS C

(75) Inventors: Ho-Seok Kwon, Suwon-si (KR); Jae-Woong Lee, Suwon-si (KR); Sun-Hwan Lee, Hwaseong-si (KR); Young-Hee Lee, Ansan-si (KR); Jeong-Ho Joo, Anyang-si (KR); Sun-Gan Chung, Suwon-si (KR); Hyun-Tae Kim, Suwon-si (KR); Eui-Hwan Cho, Seoul (KR); Hyun-Nam Myung, Seoul (KR)

(73) Assignee: Samjin Pharm. Co., Ltd., Seoul (KR)

( * ) Notice: Subject to any disclaimer, the term of this patent is extended or adjusted under 35 U.S.C. 154(b) by 287 days.

(21) Appl. No.: 12/278,659

(22) PCT Filed: Feb. 8, 2007

(86) PCT No.: PCT/KR2007/000688

§ 371 (c)(1),
(2), (4) Date: Sep. 4, 2008

(87) PCT Pub. No.: WO2007/091857

PCT Pub. Date: Aug. 16, 2007

(65) Prior Publication Data

US 2009/0023764 A1 Jan. 22, 2009

(30) Foreign Application Priority Data

Feb. 10, 2006 (KR) .................... 10-2006-0013037

(51) Int. Cl.
*A61K 31/513* (2006.01)
*A61K 31/70* (2006.01)

(52) U.S. Cl. .................... 514/274; 514/49; 514/50; 514/51

(58) Field of Classification Search .................. None
See application file for complete search history.

(56) References Cited

U.S. PATENT DOCUMENTS

| 7,429,572 | B2 | 9/2008 | Clark |
| 2005/0009737 | A1 | 1/2005 | Clark |

FOREIGN PATENT DOCUMENTS

| KR | 10-2000-0065885 A | 11/2000 |
| KR | 10-2001-0006730 A | 1/2001 |
| WO | 97/30979 A1 | 8/1997 |
| WO | 00/51990 | 9/2000 |
| WO | 00/61563 A1 | 10/2000 |
| WO | 00/61564 A1 | 10/2000 |

OTHER PUBLICATIONS

Supplemental European Search Report issued in EP 07 70 8838 on Jan. 14, 2010.

*Primary Examiner*—Brian-Yong S Kwon
(74) *Attorney, Agent, or Firm*—Sughrue Mion, PLLC

(57) ABSTRACT

A pyrimidinedione derivative of formula (I) or a pharmaceutically acceptable salt thereof exhibits excellent inhibitory activity against hepatitis C virus.

3 Claims, No Drawings

USE OF PYRIMIDINEDIONE DERIVATIVE FOR PREVENTING OR TREATING HEPATITIS C

This is a National Stage application under 35 U.S.C. §371 of PCT/KR2007/000688 filed on Feb. 8, 2007, which claims priority from Korean patent application 10-2006-0013037 filed Feb. 10, 2006, all of which are incorporated herein by reference.

FIELD OF THE INVENTION

The present invention relates to a use of a pyrimidinedione derivative or a pharmaceutically acceptable salt thereof for preventing or treating hepatitis C.

BACKGROUND OF THE INVENTION

Hepatitis C caused by hepatitis C virus (HCV) infection has been extensively studied in the last two decades, but it still remains difficult to treat due to incomplete information on HCV. At present, there is only one drug, Ribavirin, approved by Food and Drug Administration (FDA) for treating hepatitis C (Thomas et al., *Hepatology* 20(4):440, 1994), which is a purine nucleoside derivative. Interferon-α having antiviral activity against a wide spectrum of DNA and RNA viruses has been suggested as a therapeutic for hepatitis C. However, they are considered to be inappropriate for clinical application due to serious side effects and their low curative effect. Although therapy with Ribavirin-interferon-α combination has shown an improved result, it still exhibits low specificity for hepatitis C virus and low curative effect, besides the accompanying side effects such as anemia and depression. Accordingly, a new therapeutic for hepatitis C having improved curative activity and reduced side effects is required.

Some pyrimidinedione derivatives have been developed for use as an antiviral agent for treating AIDS. For example, Korean Patent Laid-open Publication 2000-65885 discloses novel pyrimidinedione derivatives synthesized by introducing a homocyclic, or alky or alkylcarbonylmethy group to the N-1 site of pyrimidinedione. The disclosure suggests that said pyrimidinedione derivatives have strong pharmacological activity against human immunodeficiency virus (HIV) in the absence of toxicity. We have unexpectedly found that such pyrimidinedione derivatives are effective in preventing or treating hepatitis C.

SUMMARY OF THE INVENTION

Accordingly, it is an object of the present invention to provide a method for effectively preventing or treating hepatitis C.

In accordance with an aspect of the present invention, there is provided a use of a pyrimidinedione derivative of formula (I) or a pharmaceutically acceptable salt thereof for preventing or treating hepatitis C:

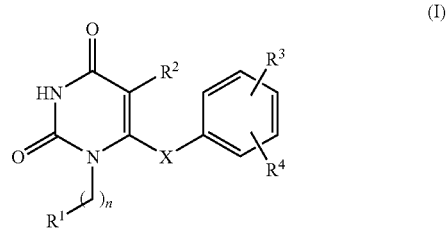

(I)

wherein,
$R^1$ is $C_3 \sim C_6$ cycloalkyl or $C_3 \sim C_6$ cycloalkenyl optionally substituted with at least one hydroxy$C_1 \sim C_4$ alkyl;
X is oxygen, sulfur or carbonyl;
n is 1 or 2; and
$R^2$, $R^3$ and $R^4$ are each independently hydrogen or $C_1 \sim C_4$ alkyl.

DETAILED DESCRIPTION OF THE INVENTION

The preferable pyrimidinedione derivative of formula (I) that maybe used in the present invention is a corresponding compound wherein $R^1$ is $C_3 \sim C_6$ cycloalkyl, cyclopentenyl or hydroxymethylcyclopentenyl.

The representative compounds for use in the present invention are listed in Table 1.

TABLE 1

| Sample No. | Name of Compounds | Structure |
|---|---|---|
| 1a | 1-cyclopropylmethyl-6-(3,5-dimethyl-phenylsulfanyl)-5-isopropyl-1H-pyrimidine-2,4-dione | 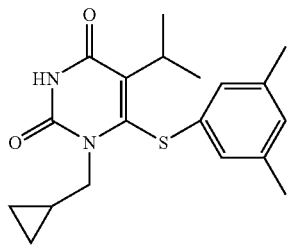 |

TABLE 1-continued

| Sample No. | Name of Compounds | Structure |
|---|---|---|
| 1b | 1-cyclopropylmethyl-6-(3,5-dimethyl-phenoxy)-5-ethyl-1H-pyrimidine-2,4-dione | 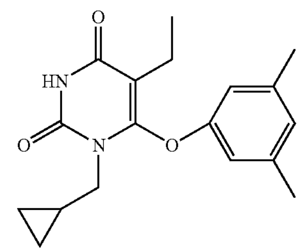 |
| 1c | 1-cyclobutylmethyl-6-(3,5-dimethyl-phenylsulfanyl)-5-isopropyl-1H-pyrimidine-2,4-dione | 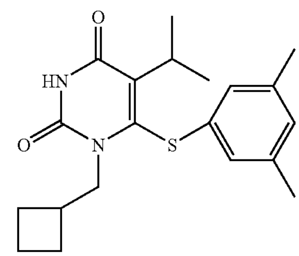 |
| 1d | 1-cyclopentylmethyl-6-(3,5-dimethyl-phenylsulfanyl)-5-isopropyl-1H-pyrimidine-2,4-dione | 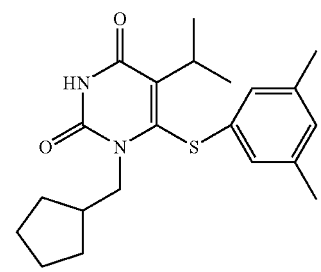 |
| 1e | 1-cyclopent-1-enymethyl-6-(3,5-dimethyl-phenylsulfanyl)-5-isopropyl-1H-pyrimidine-2,4-dione | 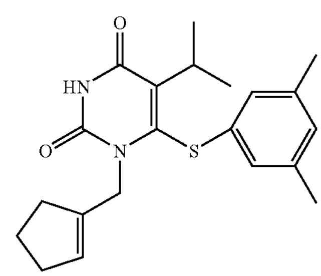 |
| 1f | 1-cyolopent-1-enymethyl-6-(3,5-dimethyl-phenoxy)-5-ethyl-1H-pyrimidine-2,4-dione | 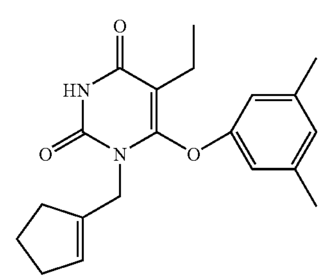 |

TABLE 1-continued

| Sample No. | Name of Compounds | Structure |
|---|---|---|
| 1g | 1-cyclopent-1-enymethyl-6-(3,5-dimethyl-phenoxy)-5-isopropyl-1H-pyrimidine-2,4-dione | 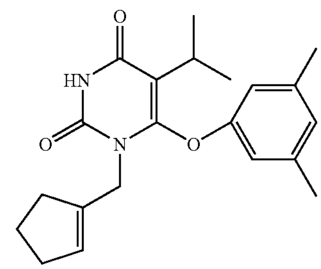 |
| 1h | 1-cyclopent-1-enymethyl-6-(3,5-dimethyl-benzoyl)-5-ethyl-1H-pyrimidine-2,4-dione | 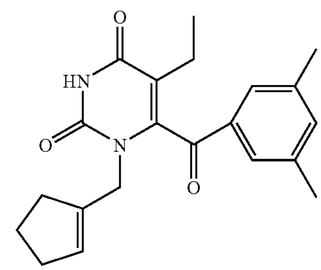 |
| 1i | 1-cyclopent-1-enymethyl-6-(3,5-dimethyl-benzoyl)-5-isopropyl-1H-pyrimidine-2,4-dione | 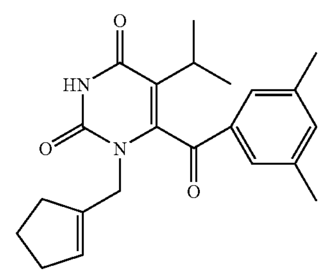 |
| 1j | 1-cyclopent-3-enymethyl-5-isopropyl-6-phenylsulfanyl-1H-pyrimidine-2,4-dione | 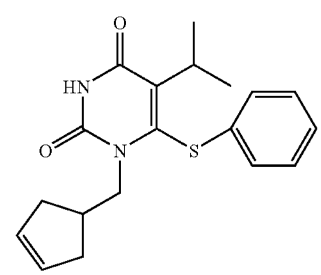 |
| 1k | 1-cyclohexylmethyl-6-(3,5-dimethyl-phenylsulfanyl)-5-isopropyl-1H-pyrimidine-2,4-dione | 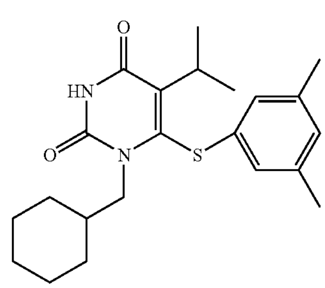 |

TABLE 1-continued

| Sample No. | Name of Compounds | Structure |
|---|---|---|
| 1l | 1-(2-cyclopentyl-ethyl)-6-(3,5-dimethyl-phenylsulfanyl)-5-isopropyl-1H-pyrimidine-2,4-dione | 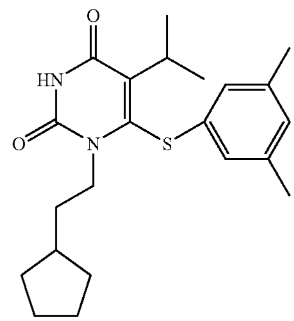 |
| 1m | 1-(2-cyclopent-2-enyl-ethyl)-6-(3,5-dimethyl-phenoxy)-5-isopropyl-1H-pyrimidine-2,4-dione | 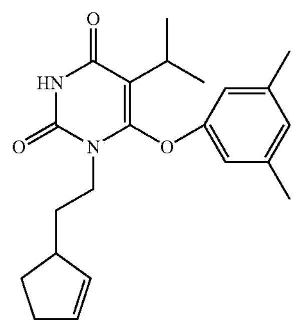 |
| 1n | 1-(2-cyclopent-2-enyl-ethyl)-6-(3,5-dimethyl-phenylsulfanyl)-5-ethyl-1H-pyrimidine-2,4-dione | 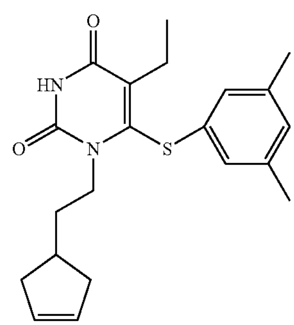 |
| 1o | 1-(2-cyclopent-2-enyl-ethyl)-6-(3,5-dimethyl-benzoyl)-5-isopropyl-1H-pyrimidine-2,4-dione | 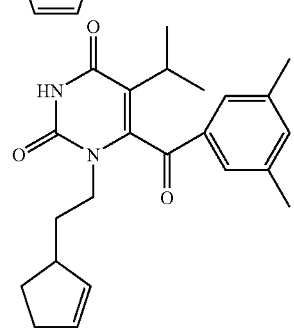 |
| 1p | 6-(3,5-dimethyl-benzoyl)-5-ethyl-1-(4-hydroxymethyl-cyclopent-1-enylmethyl)-1H-pyrimidine-2,4-dione | 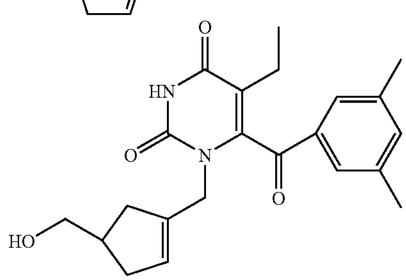 |

The pyrimidinedione derivative for use in the present invention can be prepared by the method described in Korean Patent Laid-open Publication No. 2000-65885.

For instance, the pyrimidinedione derivative for use in the present invention is prepared according to the following reaction scheme:

Reaction Scheme

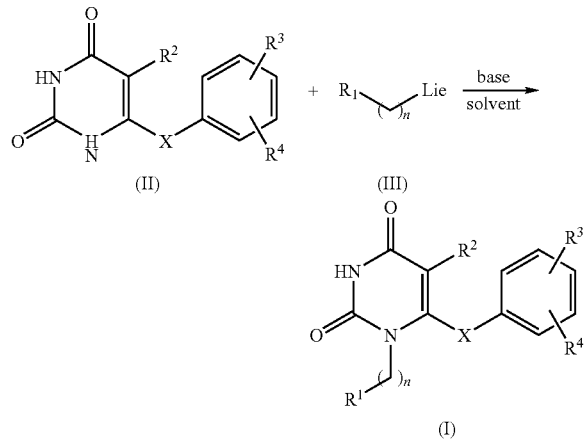

wherein, $R^1$ to $R^4$, X and n have the same meanings as defined in formula (I), and Lie means a leaving group, e.g. halogen, alkylsulfonyl and arylsulfonyl.

The compound of formula (II) used as the starting material in the reaction scheme can be prepared by a conventional method, e.g. WO 93/02044 and WO 95/18109. The pyrimidinedione derivative of formula (I) can be prepared by allowing the compound of formula (II) to react with the compound of formula (III) in the presence of a base. The equivalent ratio of the compounds of formula (II) and formula (III) preferably is in the range of 1:0.8 to 1:1.5.

The base used in the above reaction may be selected from the group consisting of anhydrous sodium hydrogen carbonate, anhydrous sodium carbonate, sodium hydride, potassium carbonate and a mixture thereof; and the organic solvent used therefor may be a polar solvent such as dimethylformamide, acetonitrile, dimethylsulfoxide and a mixture thereof. The reaction may be carried out at 10 to 100° C. for 1 to 48 hours.

Further, the pyrimidinedione derivative used in the present invention may be in the form of a pharmaceutically acceptable salt prepared by reacting a pyrimidinedione derivative (I) of formula with an inorganic or organic acid, or a base. The acid may include an organic acid such as hydrochloric acid and sulphuric acid, and an inorganic acid such as acetic acid and maleic acid. The base may include alkali or alkali earth metals such as sodium, potassium, magnesium and calcium.

According to the present invention, a pyrimidinedione derivative or a pharmaceutically acceptable salt thereof can be advantageously used for preventing or treating hepatitis C due to its capability to inhibit the activity of hepatitis C virus to an extent which is higher than the Ribavirin. Accordingly, the present invention provides a pharmaceutical composition for preventing or treating hepatitis C comprising a pyrimidinedione derivative of formula (I) or a pharmaceutically acceptable salt thereof as an active ingredient, preferably, in combination with a pharmaceutically acceptable carrier or additive.

A pharmaceutical formulation may be prepared in accordance with any of the conventional procedures. In preparing the formulation, the active ingredient is preferably admixed or diluted with a carrier, or enclosed within a carrier, sachet or other container. When the carrier serves as a diluent, it may be a solid, semi-solid or liquid material acting as a vehicle, excipient or medium for the active ingredient. Thus, the formulations may be in the form of a tablet, pill, powder, sachet, elixir, suspension, emulsion, solution, syrup, aerosol, soft and hard gelatin capsule, sterile injectable solution, sterile packaged powder and the like. Examples of suitable carriers, excipients, and diluents are lactose, dextrose, sucrose, sorbitol, mannitol, calcium silicate, cellulose, methyl cellulose, microcrystalline cellulose, polyvinylpyrrolidone, water, methylhydroxybenzoates, propylhydroxybenzoates, talc, magnesium stearate and mineral oil. The formulations may additionally include fillers, anti-agglutinating agents, lubricating agents, wetting agents, flavoring agents, emulsifiers, preservatives and the like. The composition of the present invention may be formulated so as to provide quick, sustained or delayed release of the active ingredient after their administration to a mammal by employing any of the procedures well known in the art.

Further, the present invention provides a method for preventing or treating hepatitis C in a mammal, which comprises administering the pyrimidinedione derivative of formula (I) to the mammal.

The dosage of the active ingredient may be adjusted in light of various relevant factors such as the condition of the subject to be treated, type and seriousness of illness, administration rate, and opinion of doctor. The compound of formula (I) can be administered orally or parenterally in an effective amount ranging from about 1 to 100 mg/kg (body weight), preferably 5 to 50 mg/kg (body weight) per day in case of a mammal including a human being in a single dose or in divided doses. In certain cases, an amount less than the above dosage may be suitable. An amount greater than the above dosage may be used unless it causes deleterious side effects, and such amount can be administered in divided doses per day.

The following Example is given for the purpose of illustration only, and is not intended to limit the scope of the invention.

EXAMPLE 1

To assess the effectiveness of the pyrimidinedione derivative used in the present invention as a drug for preventing or treating hepatitis C, an anti-BVDV drug screening assay was conducted with bovine viral diarrhea virus (BVDV). BVDV, a virus having a genome, reproduction cycle and infection type similar to hepatitis C virus, was employed because hepatitis C virus can not be subjected to in vivo cultivation.

(Step 1) Preparation of Cells and Virus

One day before the screening, MDBK cell line (Mardin-Darby bovine kidney, ATTC CCL22) which had been subcultured previously was trypsinized and spread on a plate, followed by counting the cell colonies formed. Then, equal amount of DMEM (Dulbecco's Modified Eagle's Medium) and Ham's F-12 were mixed, and 10% fetal bovine serum was added to the resulting mixture to prepare a tissue culture medium. The MDBK cells were inoculated to the medium at a concentration of $6 \times 10^4$ cells/ml, and then the resulting cell solution was added to a 96-well flat-bottomed plate in an amount of 100 μl per well.

Meanwhile, BVDV (ATCC VR534), which had been stored in a −80° C. freezer at a pre-determined concentration, was transferred to a biological safety cabinet and allowed to thaw at room temperature. The virus was diluted with the tissue culture medium in an sufficient amount for the virus in each well to induce 85 to 95% cell death 6 days after the virus infection.

(Step 2) Preparation of Sample Compounds

Specified pyrimidinedione derivatives (SAMJIN Pharmaceuticals) were prepared as test compounds and a conventional drug for treating hepatitis C, Ribavirin (Sigma) was used as a comparative drug. Each of the test compounds was dissolved in DMSO to prepare a sample solution. Then, the resulting sample solution was diluted with a mixture prepared by mixing equal amount of DMEM and Ham's F-12 in accordance with the three one-log series dilution to prepare sample dilutes.

(Step 3) Treating of Virus and Sample Compounds

One day after adding MDBK cells to the 96-well plate, the culture solution on the plate was removed and each of the sample dilutes obtained step 2 was added thereto, adjusting the final concentration thereof to 1 to 100 μg/ml. The comparative drug, Ribavirin, was added to each of the control wells of the palte at a concentration of 1 to 100 μg/ml.

The well-plate comprising 'cell control group well' containing MDBK cell only; 'virus control well' containing MDBK cell and BVDV virus; 'drug toxicity control well' containing MDBK cell and sample compounds for assessing the cell toxicity of each sample; 'drug calorimetric control well' containing only one of the sample compounds; and 'experimental group well' containing MDBK cell, BVDV virus and one of the sample compounds.

(Step 4) MTS Staining for Screening Plate

The well-plate had been placed in a 5% $CO_2$ incubator at 37° C. for 6 days, and then, analyzed with Cell Proliferation Assay kit (CellTiter96® $AQ_{UEOUS}$ one solution, Promega). The analysis involves the step of counting live cells by a colorimetric method and the kit contains MTS, a new tetrazolium compound which forms a stable solution when the test compounds are added, and PES, an electron coupling agent. In a cell having vigorous metabolism, NADPH or NADH generated by mitochodrial dehydrogenase renders the soluble MTS to a form of insoluble formazan crystals. Therefore, the amount of formazan crystal is directly proportional to the number of live cells in a medium.

The CellTiter96® $AQ_{UEOUS}$ one solution reagent of 10 μl was added to each well of the plate and cultivated in a incubator at 37° C. for 4 hours. Then, the plate was covered with an adhesive plate sealer, mixing formazan crystals. Absorbance of each well was measured by Molecular Devices Vmax plate reader (Molecular Devices) at 490 nm.

The toxicity of each sample compound was analyzed with a in-house computer program and the cytopathic effect (CPE), followed by calculating % cell activity, therapeutic Index (TI). The result is shown in Table 2.

TABLE 2

| Sample Compounds | MDBK/BVDV $EC_{50}(\mu M)$ | MDBK $TC_{50}(\mu M)$ | TI |
| --- | --- | --- | --- |
| 1a | 1.57 | 6.60 | 4.2 |
| 1b | 14.10 | >100 | >7.1 |
| 1c | 1.44 | 6.60 | 4.58 |
| 1d | 13.7 | >50 | >3.7 |
| 1e | 10.2 | >50 | >4.9 |
| 1f | 1.51 | >100 | >66.3 |
| 1g | 20.1 | >50 | >2.5 |
| 1h | 13.9 | 17.1 | 1.2 |
| 1i | 1.36 | 20.5 | 15.0 |
| 1j | 13.7 | >50 | >3.7 |
| 1k | 1.29 | 6.60 | 5.11 |
| 1l | 14.0 | >50 | >3.6 |

TABLE 2-continued

| Sample Compounds | MDBK/BVDV $EC_{50}(\mu M)$ | MDBK $TC_{50}(\mu M)$ | TI |
| --- | --- | --- | --- |
| 1m | 13.4 | >50 | >3.7 |
| 1n | 15.0 | >50 | >3.3 |
| 1o | 1.86 | 6.94 | 3.73 |
| 1p | 15.0 | 66.0 | 5.11 |
| Ribavirin | 1.66 | 7.00 | 4.2 |

In table 2, $EC_{50}$ means the dosage at which the desired response is present for 50% of the population, i.e., the concentration of the sample compounds at which the BVDV infection was inhibited for 50% of MDBK cells; $TC_{50}$ means the dosage at which cell death is induced for 50% of the population, i.e., the cytotoxicity of the sample compounds for MDBK cells. TI ($TC_{50}/EC_{50}$) means a comparison of the amount of a therapeutic agent that causes the therapeutic effect to the amount that causes toxic effects. Quantitatively, it is the ratio given by the dose required to produce the toxic effect divided by the therapeutic dose.

As shown in table 2, a pyrimidinedione derivative according to the present invention showed similar or superior TI value to the control drug, Ribavirin, implying that they can be used for preventing or treating hepatitis C.

While the invention has been described with respect to the above specific embodiments, it should be recognized that various modifications and changes may be made to the invention by those skilled in the art which also fall within the scope of the invention as defined by the appended claims.

What is claimed is:

1. A method for treating hepatitis C in a mammal in need of such treatment, which comprises administering a pyrimidinedione compound of the following formula (I) or a pharmaceutically acceptable salt thereof to the mammal:

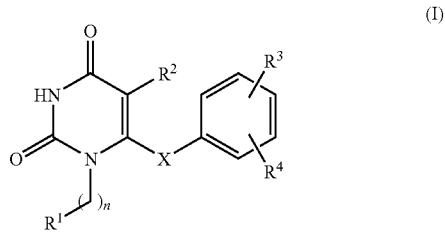

(I)

wherein, $R_1$ is $C_3~C_6$ cycloalkyl or $C_3~C_6$ cycloalkenyl optionally substituted with at least one hydroxy$C_1~C_4$ alkyl;

X is oxygen, sulfur or carbonyl;

n is 1 or 2; and $R^2$, $R^3$ and $R^4$ are each independently hydrogen or $C_1~C_4$ alkyl.

2. The method of claim 1, wherein $R_1$ is $C_3~C_6$ cycloalkyl, cyclopentenyl or hydroxymethylcyclopentenyl.

3. The method of claim 1, wherein the pyrimidinedione compound is: 1-cyclopropylmethyl-6-(3,5-dimethyl-phenylsulfanyl)-5-isopropyl-1H-pyrimidine-2,4-dione; 1-cyclopropylmethyl-6-(3,5-dimethyl-phenoxy)-5-ethyl-1H-pyrimidine-2,4-dione; 1-cyclobutylmethyl-6-(3,5-dimethylphenylsulfanyl)-5-isopropyl-1H-pyrimidine-2,4-dione; 1-cyclopentylmethyl-6-(3,5-dimethyl-phenylsulfanyl)-5-isopropyl-1H-pyrimidine-2,4-dione; 1-cyclopent-1-enylmethyl-6-(3,5-dimethyl-phenylsulfanyl)-5-isopropyl-1H-pyrimidine-2,4-dione; 1-cyclopent-1-enylmethyl-6-(3,5- dimethyl-phenoxy)-5-ethyl-1H-pyrimidine-2,4-dione; 1-cyclopent-1-enylmethyl-6-(3,5-dimethyl-phenoxy)-5-isopropyl-1H-pyrimidine-2,4-dione; 1-cyclopent-1-enylmethyl-6-(3 5 -dimethyl-benzoyl)-5-ethyl-1H-pyrimidine-2,4-dione; 1-cyclopent-1-enylmethyl-6-(3,5-dimethyl-benzoyl)-5-isopropyl-1H-pyrimidine-2,4-dione; 1-cyclopent-3-enylmethyl-5-isopropyl-6-phenylsulfanyl-1H-pyrimidine-2,4-dione; 1-cyclohexylmethyl-6-(3,5-dimethyl-phenylsulfanyl)-5-isopropyl-1H-pyrimidine-2,4-dione; 1-(2-cyclopentyl-ethyl)-6-(3,5-dimethyl-phenylsulfanyl)-5-isopropyl-1H-pyrimidine-2,4-dione; 1-(2-cyclopent-2-enyl-ethyl)-6-(3,5-dimethyl-phenoxy)-5-isopropyl-1H-pyrimidine-2,4-dione; 1-(2-cyclopent-3-enyl-ethyl)-6-(3,5-dimethyl-phenylsulfanyl)-5-ethyl-1H-pyrimidine-2,4-dione; 1-(2-cyclopent-2-enyl-ethyl)-6-(3,5-dimethyl-benzoyl)-5-isopropyl-1H-pyrimidine-2,4-dione; or 6-(3,5-dimethyl-benzoyl)-5-ethyl-1-(4-hydroxymethyl-cyclopent-1-enylmethyl)-1H-pyrimidine-2,4-dione.

* * * * *